United States Patent

Rowley et al.

[11] 4,378,009
[45] Mar. 29, 1983

[54] BRACE FOR INJURED PARTS OF THE BODY

[75] Inventors: Donald Rowley, P.O. Box 14781, Chicago, Ill. 60614; Sheldon Perlman, Chicago, Ill.

[73] Assignee: Donald Rowley, Chicago, Ill.

[21] Appl. No.: 111,847

[22] Filed: Jan. 14, 1980

Related U.S. Application Data

[63] Continuation of Ser. No. 934,903, Aug. 18, 1978, abandoned.

[51] Int. Cl.³ .............................................. A61F 5/04
[52] U.S. Cl. ......................................... 128/83; 2/24; 128/87 R; 128/325; 128/DIG. 20
[58] Field of Search ................. 128/325, DIG. 20, 83, 128/87 R, 90, 163, 169, 327; 2/16, 22, 20, 24

[56] References Cited

U.S. PATENT DOCUMENTS

| | | | |
|---|---|---|---|
| 891,181 | 6/1908 | Mitchell | 128/80 C |
| 1,667,409 | 4/1928 | Barr | 128/327 |
| 1,827,241 | 10/1931 | Kempf | 128/327 |
| 3,046,981 | 7/1962 | Biggs, Jr. et al. | 128/80 C |
| 3,454,010 | 7/1969 | Lilligren et al. | 128/327 |
| 3,454,963 | 7/1969 | Palladino | 2/24 |
| 3,570,495 | 3/1971 | Wright | 128/327 |
| 3,667,462 | 6/1972 | Moon | 128/169 |
| 3,934,583 | 1/1976 | Hollingshead | 128/80 C |
| 4,219,892 | 9/1980 | Rigdon | 128/DIG. 20 |

*Primary Examiner*—Robert W. Michell
*Assistant Examiner*—J. L. Kruter

[57] ABSTRACT

An elongated, elastic tube provides a brace for wrapping about a person's knee or other part of the body. The brace is wrapped about the knee in a criss-cross fashion wherein four diagonal members intersect at four points surrounding the knee cap, i.e., top, bottom and each side. The brace is held in place by tape, VELCRO or other fastening means, and may be solid or inflated with air or another suitable fluid until a comfortable, protective pressure is reached within the elongated tube. When properly positioned and filled, the brace supports the knee or other body member, and also provides a protective cover which withstands otherwise injurious impacts. The basic wrap may be incorporated into a single unit having a criss-cross wrap outline integrally formed and adapted to be wrapped in a single unit.

10 Claims, 11 Drawing Figures

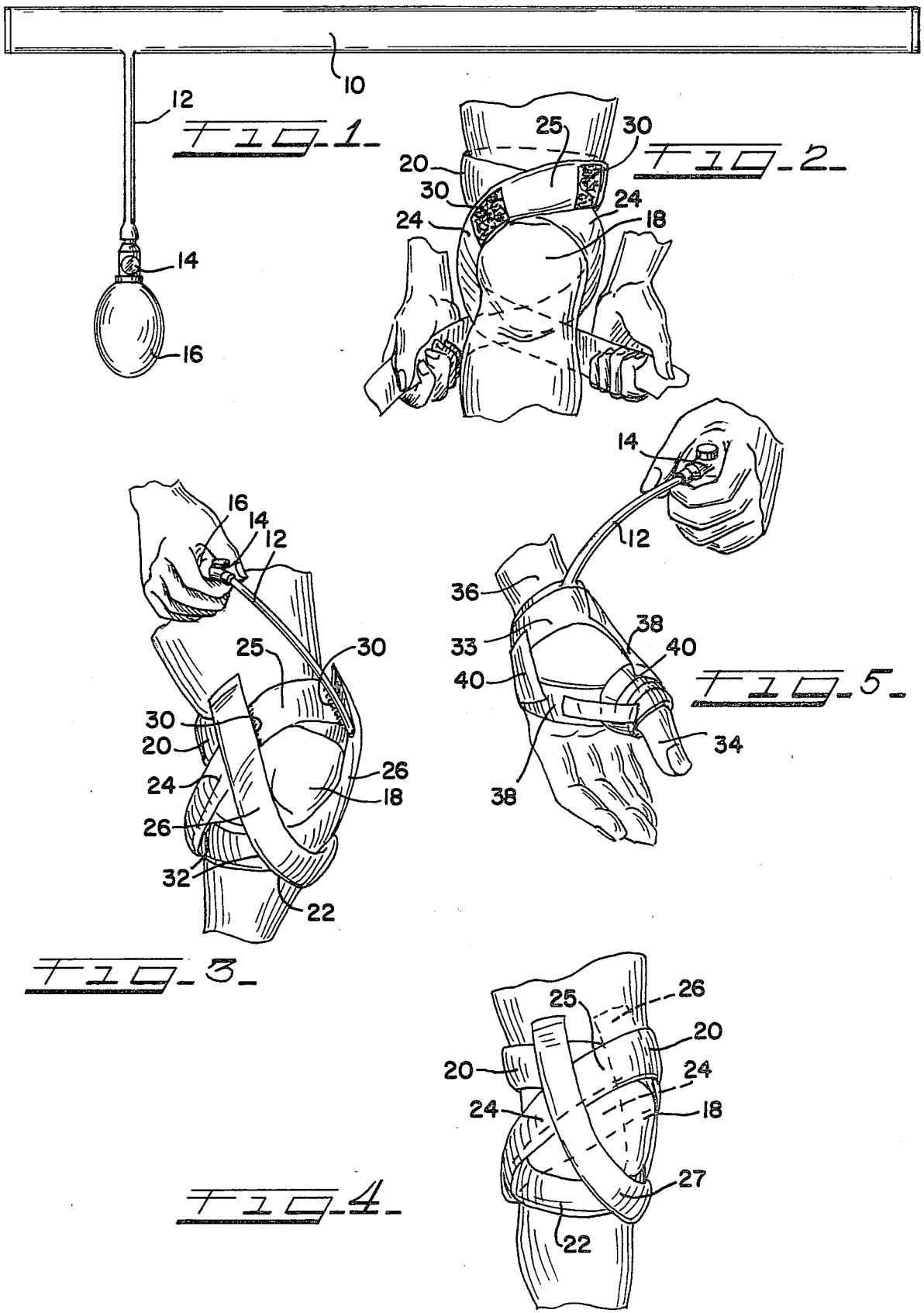

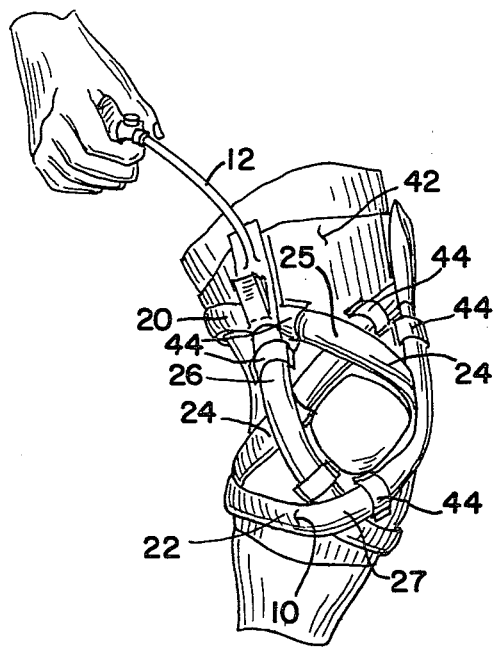
FIG_6_
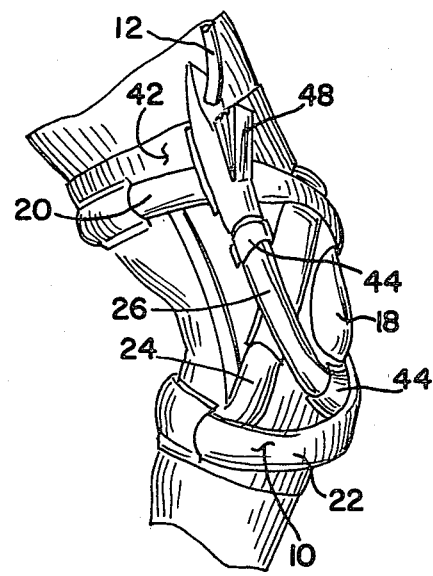
FIG_7_
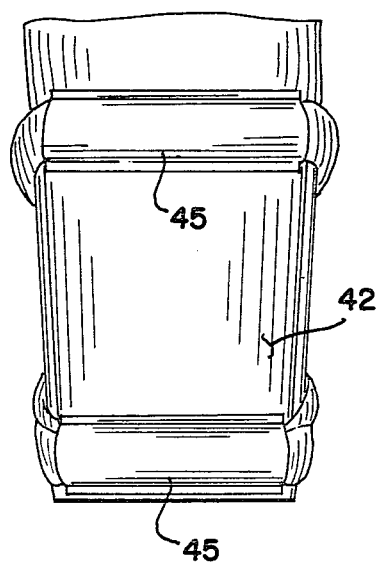
FIG_8_
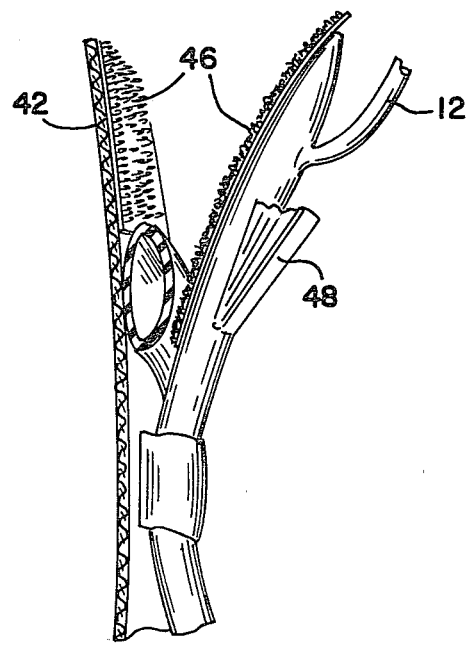
FIG_9_

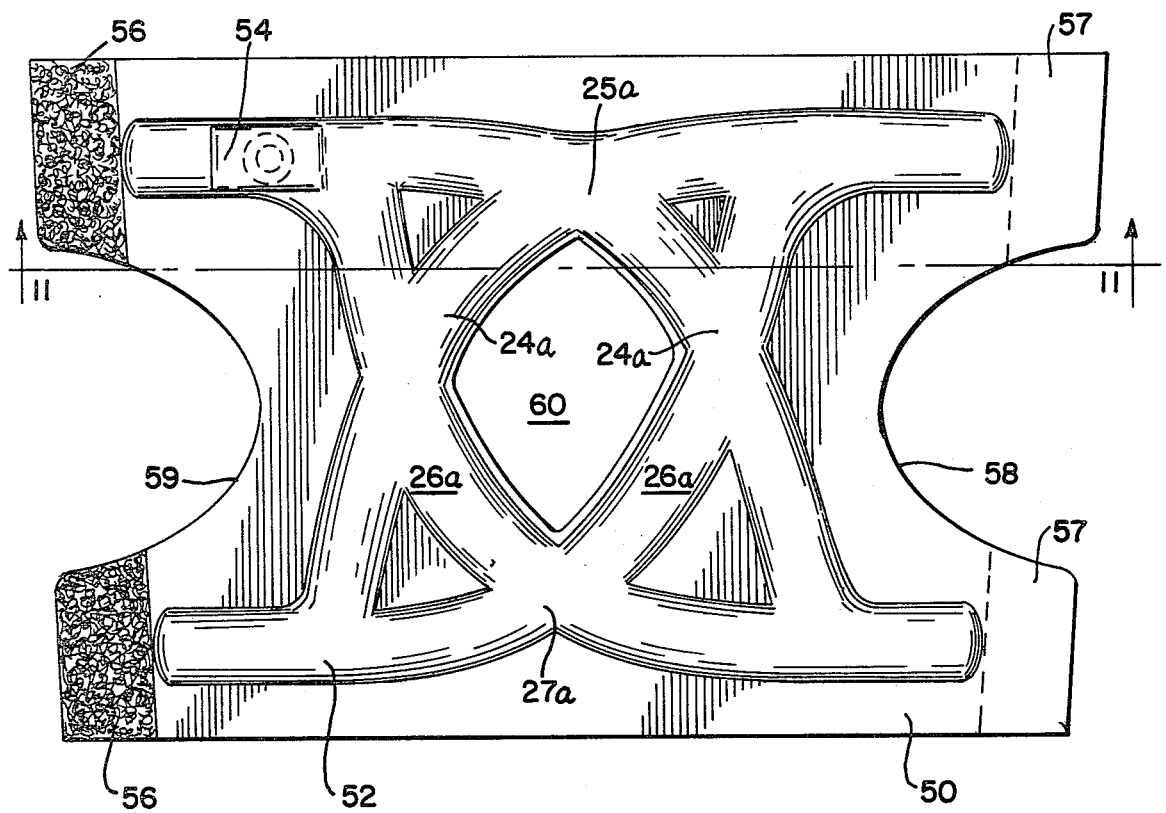
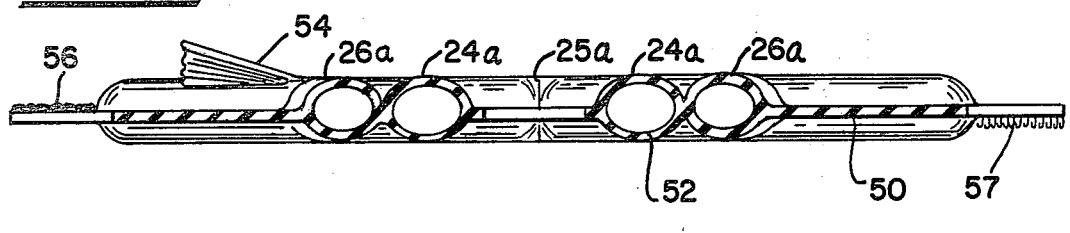

BRACE FOR INJURED PARTS OF THE BODY

This application is a continuation of application Ser. No. 934,903 filed Aug. 18, 1978 now abandoned.

BACKGROUND OF THE INVENTION (1) Field of the Invention

This invention pertains to a wrap type brace worn by persons having injuries to an extremity. The device is preferably used as a knee brace but can be modified and used as a wrist or hand brace to protect these members of the body which have been fractured, sprained, broken or otherwise injured, and which must be not only held in place during healing, but also protected in the event that the person desires to be active.

(2) Description of the Prior Art

Prior art knee braces and the like have generally been comprised of typical elastic bands that are wrapped around the knee and held in place with metal clips. More expensive versions of this basic knee brace include elastic braces having metal stiffeners and hinged bars extending along each side of the person's knee and at least theoretically provide lateral support to keep the knee in position during activity, yet allow the knee to pivot. These braces have not met with widespread acceptance and use because they have been ineffective, costly, cumbersome and do not provide both support and protection to the wearer.

SUMMARY OF THE INVENTION

This invention pertains to an elastic tube member that may be wrapped about a portion of a person's body, for example, a knee, in such a fashion as to provide not only support for holding the wrapped portion in place, but also provides protection because of the bumper, shock-absorbing effect of the tube once it is properly positioned.

In particular, when used as a knee brace, which is the preferable mode of use, the elastic tube may initially be wrapped at least once about the person's leg above or below the knee cap. When initially wrapped above the knee cap, the elastic tube is positioned at the back of the leg and is then brought around to the front of the knee where it is criss-crossed. Next the tube is brought diagonally alongside and behind the person's knee to a position on the other, lower side of the knee cap at the back of the leg where it is once again criss-crossed, brought forward and wrapped at least once around the leg. Lastly, the tubing is then extended diagonally alongside the outer portion of the person's leg and extended upwardly to attach with the initial wrap above the knee. Tape, snaps, or any other suitable type of attachment may be used to hold the ends of the tube in place after the wrapping is completed.

During wrapping, the elastic feature of the tube is utilized in order that the amount of holding can be varied by adjusting the tension in the wrap. After the end is held in place with tape or the like, the sides may be taped at their points of intersection to ensure that the side wraps are securely held in place and will not slip or roll during wearer's activity. The tape may be attached along the outer and inner portions of the knee wrap to ensure that the tubing is securely held in place. It is also contemplated that an elastic stocking or the like could be used to mount the wrap and/or pulled over the tubing after it is attached about the knee to also provide the necessary stability and prevent so-called rolling of the wrap.

After positioning the elastic tubing and firmly securing it in position, it may be inflated with air or any other suitable fluid that will naturally expand the tubing and tighten it about the wearer's knee. The tubing can be filled by using a small, portable, hand-held inflating bulb. The tubing could be provided with a valve and filled by using a compressor or the like. A release valve may be utilized to assure that pressurized fluid only up to a certain point would be allowed to enter before being released in order to provide a safety feature for the wearer. It is contemplated that after over-inflating the knee brace, the wearer may manually release some of the pressure until a comfortable volume, pressure, and feel is obtained from the knee brace.

Once in place, there are provided four points of intersection of the tubing. These points are spaced 90° about the knee on the top, bottom, and each side, thus providing four pressure points for securely holding the knee and for keeping the knee cap securely in place.

A smaller version of the knee brace tubing may be provided in order to provide the same features of the wrap and inflation characteristics and used on a person's broken or sprained wrist, fingers, elbow and the like.

An object of the disclosure is to provide a brace for healing of broken or injured parts of the body, specifically the legs, knees, hands, neck, shoulder and arms.

It is yet another object of the disclosure to provide a hollow, elastic tubing, having a valve for admitting air into the tubing and which can be shut off to retain air after a comfortable pressure is obtained within the tubing that is wrapped about a portion of the wearer's body.

It is yet another object of this disclosure to provide an improved knee brace that may be wrapped around the person's knee in such a fashion as to provide four point concentrated support to maintain a knee securely in position by wrapping the tubing above and below a person's knee and criss-crossing the tubing along each side of the wearer's knee to thus provide both horizontal and vertical support to maintain the knee in position for healing and to prevent injury during every-day activities and during athletic events.

Another object of this disclosure is to provide a sock with the elastic, knee supporting tubing attached in an adjustable fashion.

It is yet another object of this disclosure to provide a knee brace or brace for other parts of the body having a release valve to allow pressure to be released from the inflatable tubing.

Another object of this disclosure is to provide a knee brace in the form of a flexible wrap having integrally formed support ribs or tubes and which may be easily and quickly attached to the wearer's leg.

These and other objects of the invention will become apparent to those having ordinary skill in the art with reference to the following drawings, description and appended claims.

BRIEF DESCRIPTION OF THE DRAWINGS

FIG. 1 is a plan view of the elongated tubing, filling valve and air supply described in this disclosure;

FIG. 2 is a view showing a knee being wrapped with the brace of this disclosure;

FIG. 3 is a view showing the tubing wrapped in place and being filled with fluid;

FIG. 4 is a side view similar to FIG. 2 showing the brace on a person's knee;

FIG. 5 is a modification showing the use of a smaller sized, elongated, inflatable tubing for use in setting or protecting injured or broken hand or wrist members;

FIG. 6 shows tubing attached to an elastic sock-type member;

FIG. 7 is a side view of the device shown in FIG. 6;

FIG. 8 is a rear view of the tubing and sock shown in FIG. 6;

FIG. 9 shows a means for securing one free end of the tubing, and shows a bellows-type pump and fluid release valve;

FIG. 10 shows tubing integrally formed with a sheet-type member which can easily be wrapped around an injured knee; and FIG. 11 is a sectional view taken generally along lines 10—10 of FIG. 10.

DETAILED DESCRIPTION

Referring now to the drawings and, in particular, FIG. 1, there is shown an elongated tube 10, which is circular in diameter when inflated in the free form, much like a bicycle innertube. Extending from tubing 10 is a flexible stem 12 with a manually releasable filling valve 14 connected with an associated filling bulb 16. In the form shown in FIG. 1, when the valve 14 is open, air may flow freely from the bulb 16 through stem 12 and tube 10 for filling purposes. Once a desirable pressure or position is reached, valve 14 is simply turned off and air cannot flow out of the tube 10. It is also contemplated that shut-off valve 14 may include an automatic release feature that would prevent tube 10 from being filled to an undesirable or dangerously high pressure which could result in injury from bursting or from fitting too tightly about a portion of a person's body.

As shown in FIG. 2, the elongated tube 10 is preferably used as a knee brace. The knee has a particular structure that is complicated. The knee functions to join a large leg bone called the femur or thigh bone with a large bone of the lower leg called the tibia. The knee acts as a hinge connecting these bones. However, it is not an ordinary hinge, but a hinge that must bend, rotate, slide and float and withstand tremendous forces, which naturally and normally pass through the legs. To hold the knee together, there are four ligaments, two on each side of the knee and two that criss-cross and run up through the center of the knee joint. Cartilage, on the other hand, is a soft, disc-like material between the joints that acts like a shock absorber. Thus, the ligaments hold the knee elements in place, and the cartilage functions to provide cushioning benefits.

As is known to spectators and participants of athletics the knee is not well suited for its frequent use where not only extreme pressures are brought to bear on the knee, but frequently excessive impacts, bruising and contact with the knee occurs. In particular, both cartilage and ligament injuries occur. When injuries occur, the ligaments are pulled or strained, or cartilage is ruptured, thus causing the knee to be flexible and not held in place and being very irritating. The knee brace disclosed herein compensates for damaged cartilage or ligaments by securely holding the knee cap and leg bones in their natural position and yet allowing a high degree of movement.

As shown in FIG. 2, the elongated tube may be initially wrapped above the knee 18 into what is called an upper wrap 20. The upper wrap 20 is simply one or more turns of the elongated tube 10 followed by an enclosure below the knee in what is called a lower wrap 22. Interconnecting upper and lower wraps 20, 22 respectively is a pair of so-called upper diagonals 24 which extend downwardly from the front, top of knee 18 at point 25 to the lower wrap 22. After the leg is wrapped below the knee, tubing 10 is extended upwardly to form lower diagonals 26 which extend from point 27 below the knee 18 to the upper wrap 20.

As shown in FIG. 3, when the wrap has been completed, the ends of the elongated tube 10 may be held in place by tape, snap, or a VELCRO type connection 30. Tape may be applied alongside the knee brace at points 32 (FIG. 3) to provide lateral support interconnecting the upper and lower wraps 20, 22, to prevent so-called rolling.

After the wrap is formed in the position shown in FIGS. 2-4, it may then be filled with fluid by simply pumping air from the flexible bulb 16 or from any convenient air source as may be provided with a compressor, mechanical pump, bellows, or the like. It is also contemplated that other fluids may be desirable for use with the knee brace in the event that additional shock-absorbing features are necessitated, and a heated water or the like could also be circulated through the tube to provide a therapeutic massage, as well as shock-absorbing and rigidifying features.

When in position as shown in FIG. 3, and filled with air, the elongated tube 10 will naturally expand and further compress about the knee 18. It is suggested that the tube be initially over inflated and then deflated as required by the wearer after moving about to customize the fit. When filled with fluid, including air, the increased pressure and holding forces encircling the leg above, below, and alongside the knee provide support to the knee members including the patella, or knee cap, cartilage and ligaments. The diagonals 24, 26, by interconnecting the upper and lower wraps 20, 22, pull the wraps toward one another and provide equal and opposite forces extending laterally and vertically toward the knee cap to hold the knee cap and supporting members such as cartilage and ligaments securely in position for healing and support.

A modification of the knee wrap and its elongated tube 10 is shown in FIG. 5 where a smaller version is adapted to be wrapped about a person's hand for setting broken or sprained tumbs, wrists, fingers and the like. As was done with the knee brace, the wrap may be positioned about the wrist at 33 and then extended to a thumb 34, back to the wrist 36, and interconnected with so-called diagonals 38. Tape or other connectors such as snaps, buckles or the like 40 securely hold the wrap in position. Thus the wrist wrap 33 acts as an anchoring means for the diagonals 38 which extend to the thumb 34. When attached, the tubing forms a rigid, unitary structure which holds the thumb in place to aid in healing.

FIG. 6 shows a modification of the basic design just disclosed where an elastic sock 42 provides a mounting surface for the tubing that reinforces the knee. The elastic sock has the elongated tube 10 permanently attached thereto by side hold-downs 44 (FIG. 7) and upper and lower rear hold-downs 45 (FIG. 8). The hold-downs are attached to the elastic sock 42 and fitted loosely about the tubing 10 to allow it to move thereunder until a comfortable, customized fit is obtained. As shown in FIGS. 6, 7 and 9, each end of tubing 10 is designated 46 and is shown with a VELCRO or other convenient means for use in securely holding down the end portions of the tubing 10. The tubing 10 as used may be a solid piece of elastic material that can be pulled and lengthened to increase the tension and holding power of tubing around the wearer's knee. On the other hand, the tubing 10 can be hollow and of such a design as to be filled by a hand pump through filling stem 12. The tubing 10 may include an integrally formed or integrally attached bellows 48 as shown in FIG. 9. Thus, by adjusting the length tension is induced into the elastic member which increases its holding power. Thus the attachment portions or ends 46 should be allowed a sufficient length as to compensate for a certain degree of tension and insure that a secure fastening of the ends occurs.

The wrap shown in FIG. 6 may be easily placed on a wearer and is intended to be a customarized version which may be easily attached and removed. Thus, it can be seen that in customizing the fitting of the wrap shown in FIG. 6, elastic sock 42 would initially be placed over the wearer's knee. Then the tubing 10 would be pulled or tensioned in a customized fashion depending on the height and leg dimension of the wearer. When properly located, the side hold-downs 44, and rear hold-downs 45, would be marked and later securely attached so as to provide a customarized unit for the wearer. As shown in FIG. 6, it is also anticipated that the center portion of the elastic sock 42 be cut out to allow the knee cap to more or less float between the support provided by the upper and lower diagonals 24, 26 respectively.

Another modification of the disclosure is shown in FIG. 10 wherein an integrally formed unit is provided. A sheet of plastic material such as a vinyl 50 has a number of integrally formed tubes 52 located therein. Tubes 50 are such a design as to duplicate the diagonals 24, 26 described with respect to the two earlier versions. Thus by integrally forming tubing sections shown as 24a and 26a, the upper and lower diagonals of the earlier models are also duplicated.

In use, the modular unit of FIG. 10 is merely placed over the wearer's leg and tightened in such a fashion that a comfortable, supportive fit is obtained. It is also anticipated that the vinyl material will have a certain amount of elasticity in order to enable it to be stretched or placed in tension to provide radial, supportive forces to the wearer's knee. Once in place, the ends 56 and 57 are securely attached. After this initial attachment about the knee the integral tube members 52 may be filled with a fluid such as air. As the tubes 52 are filled with air they will expand inwardly and apply additional supportive forces to the wearer's knee duplicating the forces provided by the manually wrapped units shown in FIG. 2 and the customized version shown in FIG. 6. It is also contemplated that the tubing members 52 may be solid members and not hollow. Thus, by merely placing the wrap around the wearer's knee and securely tightening it, the integrally formed solid tubing would provide sufficient forces for supporting and protecting the knee.

End cutouts 58, 59 extend into the sheet 50. By removing material, the back of the knee is allowed to flex once the wrap is secured in place. As shown in FIG. 10, it is also contemplated that the middle portion 60 of sheet 50 be removed to allow the knee to extend therethrough in order that flexing movement of the knee is permitted.

As shown by the foregoing, a new and different knee brace is provided. This knee brace is highly portable and provides a multi point force application about a wearer's knee which holds the leg and knee components and bones securely in position for healing while allowing a certain degree of movement and/or activity although the knee is injured.

The foregoing description and drawings merely explain and illustrate the invention and the invention is not limited thereto, except insofar as the appended claims are so limited, as those who are skilled in the art and have the disclosure before them will be able to make modifications and variations therein without departing from the scope of the invention.

What is claimed is:

1. A brace for supporting an injured portion of a person's body, the improvement comprising:
    flexible means;
    said flexible means comprising means for wrapping about a portion of the body and having means for fastening to secure the flexible means in place;
    said flexible means comprising an elastic member for stretching to thereby provide a holding force for securing the flexible means in place and to securely hold the injured portion in place for healing;
    wrapped means having means encircling the body at two points adjacent the injured portion
    said flexible means comprising a sheet having integrally formed tube means;
    said integrally formed tube means providing upper and lower wrap tubes;
    diagonal means having means extending to interconnect the wrapped means encircling the body and with means intersecting one another;
    said means intersecting providing support points and concentrated forces for holding the body in position for healing;
    diagonal members formed integrally with the flexible means and extending to interconnect the upper and lower wrap tubes in a diagonal fashion whereby the diagonal means criss-cross and intersect to provide points of reinforcement for treating the injured portion of the body during healing.

2. The brace of claim 1 wherein the integrally formed means comprise:
    hollow tube members;
    means for admitting a fluid into the hollow tube portion and pressurizing the same for rigidifying the flexible means;
    valve means for holding pressurized fluid within the hollow tubes and selectively emptying the pressurized fluid from the tubes.

3. The flexible wrap of claim 2, comprising:
    a flexible sheet adapted to be wrapped about a knee and including:
    end means with connecting means for interconnecting in a tight fashion about a person's knee;
    said wrap having an opening disposed to fit about a person's knee;
    said diagonals including means extending adjacent the openings to provide a four point rigidified framing structure about the opening.

4. A brace for joint of the body comprising:
    continuous, hollow, inflatable, elastic tubing adapted for surrounding a joint of the user;
    said tubing having four intersecting points spaced at approximate 90 degree intervals for adaptation about the front of the joint;

said tubing providing an opening at the front so that the joint may be extended therethrough;

said tubing providing another opening at the back of the joint;

means for securing said intersecting tubing about the joint; and means for inflating said tubing with a fluid to increase the pressure exerted about the joint by the intersecting tubing.

5. A brace as described in claim 4 wherein said four intersecting points occur at the top, right side, bottom, and left side of the front of the joint.

6. A brace as described in claim 4 wherein said continuous, hollow, inflatable, elastic tubing is provided with a valve having an automatic release feature for preventing over-inflation of the tubing.

7. A brace as described in claim 4 wherein said continuous, hollow, inflatable, elastic tubing is:
an elongated member for wrapping around the joint;
said elongated member having two ends;
said elongated member being provided with holding means for holding said ends in place after said elongated member is wrapped around the joint.

8. The brace as described in claim 4 wherein said continuous, hollow, inflatable, elastic tubing is mounted on an elastic sock.

9. The brace as described in claim 8 wherein said sock is provided with hold-down loops for mounting said elastic tubing.

10. The brace as described in claim 4 wherein said tubing is formed as part of a flexible sheet;
said flexible sheet being adapted to be wrapped about the joint.

* * * * *